United States Patent
Ortiz et al.

(10) Patent No.: US 8,133,249 B2
(45) Date of Patent: Mar. 13, 2012

(54) DEVICES AND METHODS FOR STRICTURE DILATION

(75) Inventors: Mark Ortiz, Milford, OH (US); Jeffrey Swayze, Hamilton, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 1694 days.

(21) Appl. No.: 11/161,266

(22) Filed: Jul. 28, 2005

(65) Prior Publication Data

US 2007/0027467 A1 Feb. 1, 2007

(51) Int. Cl.
*A61M 29/00* (2006.01)
(52) U.S. Cl. ........................................ 606/191
(58) Field of Classification Search ............ 606/27–52; 607/100–102, 115–126; 128/898, 653.4, 128/656, 658; 600/373, 435, 433
See application file for complete search history.

(56) References Cited

U.S. PATENT DOCUMENTS

| | | | |
|---|---|---|---|
| 5,456,667 A | 10/1995 | Ham et al. | |
| 5,665,103 A | 9/1997 | Lafontaine | |
| 5,674,242 A | 10/1997 | Phan et al. | |
| 5,800,517 A | 9/1998 | Anderson et al. | |
| 6,033,397 A * | 3/2000 | Laufer et al. | 606/27 |
| 6,312,407 B1 | 11/2001 | Zadno-Azizi et al. | |
| 6,485,458 B1 | 11/2002 | Takahashi | |
| 6,514,237 B1 | 2/2003 | Maseda | |
| 6,667,825 B2 | 12/2003 | Lu et al. | |
| 6,872,433 B2 | 3/2005 | Seward et al. | |
| 7,530,979 B2 * | 5/2009 | Ganz et al. | 606/41 |
| 2003/0158550 A1 | 8/2003 | Ganz et al. | |
| 2003/0236531 A1 | 12/2003 | Couvillon | |
| 2004/0098081 A1 | 5/2004 | Landreville et al. | |
| 2005/0096721 A1 | 5/2005 | Mangin et al. | |
| 2005/0102017 A1 | 5/2005 | Mattison | |
| 2005/0165439 A1 | 7/2005 | Weber et al. | |
| 2007/0027519 A1 | 2/2007 | Ortiz et al. | |
| 2007/0247033 A1 | 10/2007 | Eidenschink et al. | |
| 2007/0299422 A1 | 12/2007 | Inganas et al. | |

FOREIGN PATENT DOCUMENTS

| | | |
|---|---|---|
| JP | 2000-217927 A | 8/2000 |
| WO | 2004/000403 A1 | 12/2003 |
| WO | 2004/030554 A1 | 4/2004 |
| WO | 2004/069169 A2 | 8/2004 |
| WO | 2004/103220 A2 | 12/2004 |
| WO | 2005/072809 A1 | 8/2005 |

OTHER PUBLICATIONS

CN Application No. 200610108909.4, Office Action mailed Sep. 25, 2009.
Australian Office Action issued Jun. 29, 2011 for Application No. 2006203216 (4 pages).
Extended European Search Report issued Oct. 18, 2006 for Application No. 06253931.7 (6 pages).
European Office Action issued Jun. 10, 2008 for Application No. 06253931.7 (5 pages).
Japanese Office Action issued Jul. 12, 2011 for Application No. 2006-205094 (4 pages).

(Continued)

*Primary Examiner* — Kevin T Truong (57) ABSTRACT

Various methods and devices for dilating strictures in a lumen are provided. In an exemplary embodiment, a stricture dilation device is provided having an elongate shaft with at least one electrically expandable actuator coupled thereto and adapted to radially expand to dilate a stricture in a lumen.

25 Claims, 7 Drawing Sheets

OTHER PUBLICATIONS

Bar-Cohen, Y, Electroactive polymers as artificial muscles—capabilities, potentials and challenges. Nondestructive Evaluation and Advanced Actuators Technologies, Jet Propulsion Laboratory, NASA. 2000, 9 pages.

* cited by examiner

DEVICES AND METHODS FOR STRICTURE DILATION

FIELD OF THE INVENTION

The present invention relates broadly to surgical devices, and in particular to methods and devices for dilating strictures.

BACKGROUND OF THE INVENTION

Bariatric surgery is a treatment for morbid obesity that involves alteration of a patient's digestive tract to encourage weight loss and to help maintain normal weight. One common type of bariatric surgery is gastric bypass surgery which aims to decrease the size of a patient's stomach. In particular, the stomach is divided into upper and lower pouches using a stapler and/or stitches. The jejumum (the middle section of the small intestine) is also divided into two parts. One part of the jejunum (called the "Roux limb") is brought up behind the colon and lower stomach pouch, and joined or "anastamosed" to the upper stomach pouch. The remaining end of the jejunum is attached to the side of the Roux limb. As a result, a new digestive pathway is created, where food travels down the esophagus, into the upper stomach pouch, and through the anastamosis into the Roux limb. Digestive juices from the stomach, the liver, and the pancreas travel through the lower stomach pouch, down the duodenum and jejunum, and into the Roux limb where the two parts of the jejunum are attached and further digestion takes place.

While effective, gastric bypass surgery is not without complications. For example, scar tissue can develop in the stoma (the junction between the upper stomach pouch and the Roux limb), creating a stricture which can make digestion difficult. As a result, further surgery needs to be performed to remove the stricture. Several devices are available for dilating strictures. For example, a tube can be inserted down the patient's esophagus and manipulated to break up the tissue surrounding the stricture. While this can be effective, it can be difficult to fully re-open the stricture. The procedure can also be very time-consuming. Another common device used to dilate strictures is a balloon catheter that is inserted down the patient's esophagus to position the deflated balloon within the stricture. The balloon is then expanded to expand the stricture, thereby re-opening the passageway. Balloon catheters can be effective, however the balloon can break when expanded against the stricture.

Accordingly, there is a need for improved methods and devices for dilating strictures.

BRIEF SUMMARY OF THE INVENTION

The present invention generally provides various methods and devices for dilating strictures. In one exemplary embodiment, a tissue dilation device is provided that has a substantially flexible elongate shaft with a proximal end coupled to a handle and a distal end having an actuator disposed around a distal portion thereof. The actuator is adapted to radially expand upon delivery of energy thereto to dilate a stricture.

The actuator can have a variety of configurations, and it can be formed from a variety of materials. In one exemplary embodiment, the actuator can be an electrically-expandable member, and more preferably it can be in the form of an electroactive polymer (EAP). For example, the actuator can be in the form of a fiber bundle having a flexible conductive outer shell with several electroactive polymer fibers and an ionic fluid disposed therein. Alternatively, the actuator can be in the form of a laminate having at least one flexible conductive layer, an electroactive polymer layer, and an ionic gel layer. Multiple laminate layers can be used to form a composite. The actuator can also include a return electrode and a delivery electrode coupled thereto, with the delivery electrode being adapted to deliver energy to the actuator from an external energy source.

Methods for dilating strictures are also provided. In one exemplary embodiment, the method can include inserting a substantially flexible elongate shaft into a lumen, and positioning an actuator disposed on a distal portion thereof within a stricture formed in the lumen. The actuator can then be electrically actuated to expand radially, thereby increasing a diameter of the stricture. While the actuator can have a variety of configurations, in one exemplary embodiment the actuator is substantially cylindrical and it is adapted to expand at least about 30% in size when energy is delivered thereto.

BRIEF DESCRIPTION OF THE DRAWINGS

The invention will be more fully understood from the following detailed description taken in conjunction with the accompanying drawings, in which.

DETAILED DESCRIPTION OF THE INVENTION

Certain exemplary embodiments will now be described to provide an overall understanding of the principles of the structure, function, manufacture, and use of the devices and methods disclosed herein. One or more examples of these embodiments are illustrated in the accompanying drawings. Those of ordinary skill in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

Disclosed herein are methods and devices for dilating strictures in lumens, such as the stoma, carotid arteries, peripheral vessels, urethra, esophagus, bile duct, jejunum, and duodenum. In an exemplary embodiment, a device can include one or more actuators coupled thereto and adapted to radially expand. In use, the radial diameter of the actuator can expand to effect dilation of a stricture. A person skilled in the art will appreciate that the methods and devices disclosed herein can have a variety of configurations, and they can be adapted for use in a variety of medical procedures. For example, the methods and devices can be used in the blood vessels after a stenosis has been compressed by percutaneous transluminal coronary angioplasty (PTCA), percutaneous transluminal angioplasty (PTA), or removed by atherectomy or other means, to help improve the results of the procedure and reduce the possibility of restenosis. Moreover, the methods and devices disclosed herein can be used with any other procedures known in the art that require the dilation of strictures. The stricture dilation device can also be incorporated into a variety of other devices to allow stricture dilation to be performed in conjunction with other procedures.

Figure 1A:
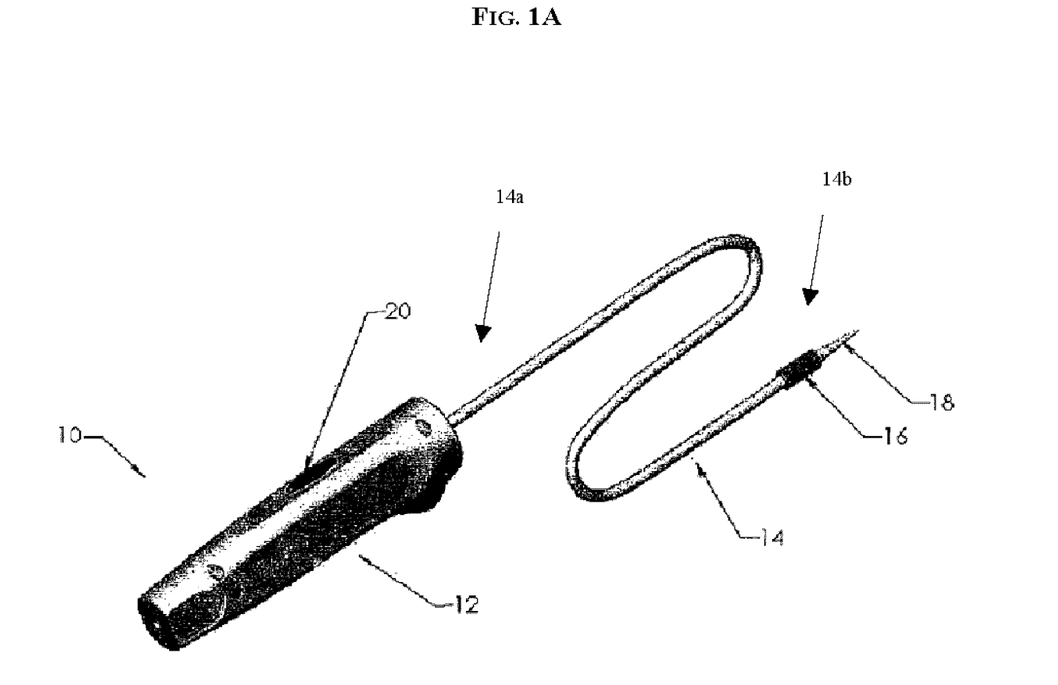
FIG. 1A is perspective view of one exemplary embodiment of a stricture dilation device.
Figure 1B:
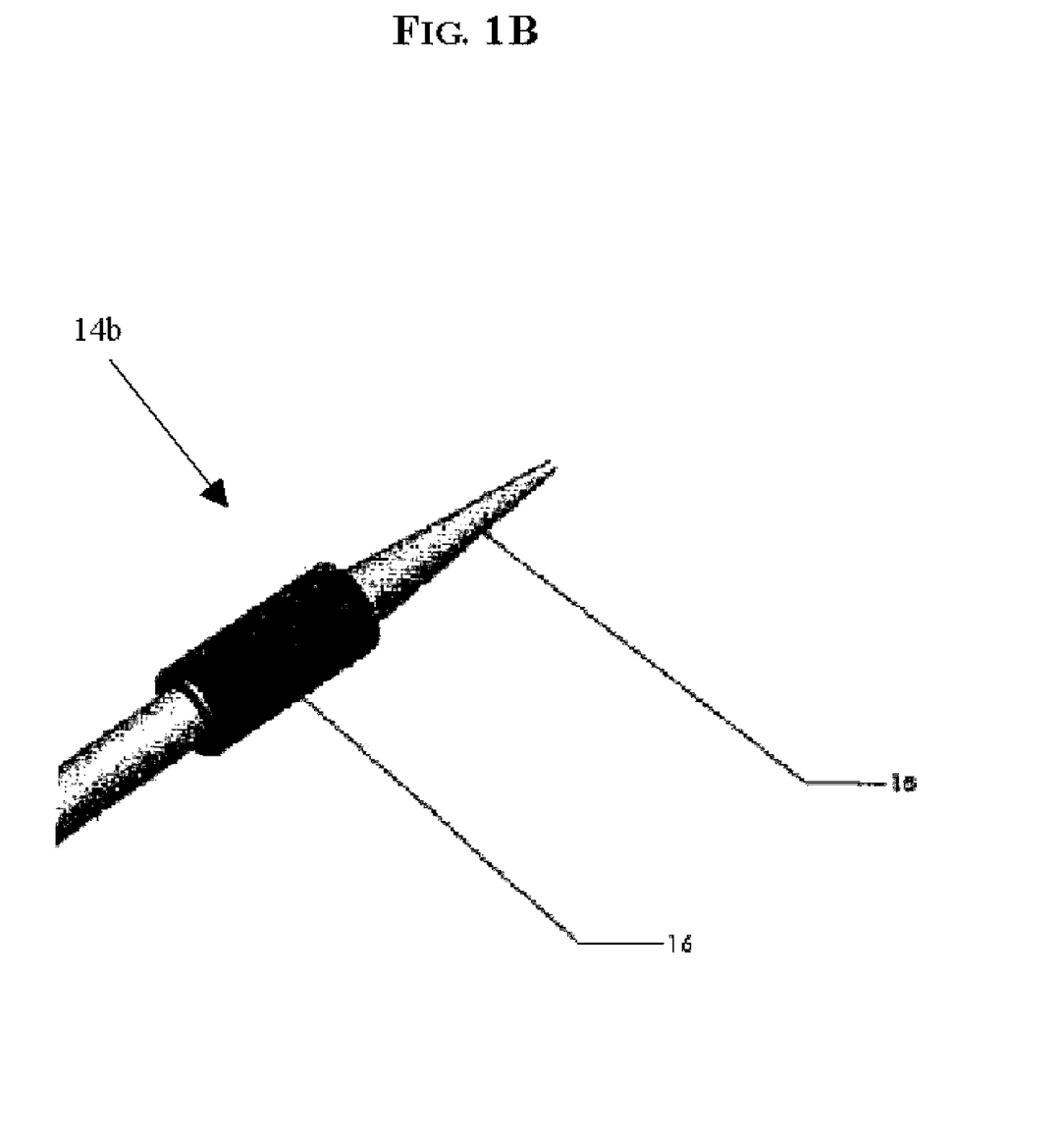
FIG. 1B is a perspective view of the distal portion of the stricture dilation device shown in FIG. 1A showing an actuator disposed thereon.
Figure 1C:
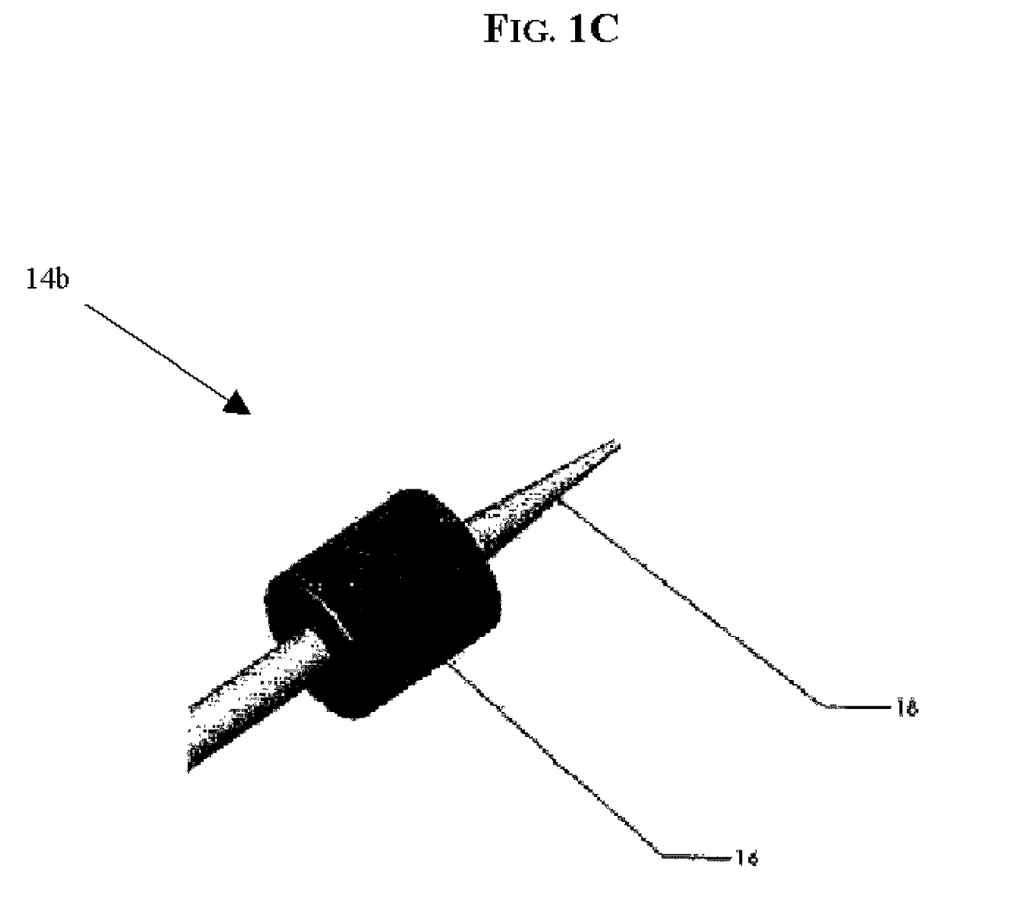
FIG. 1C is a perspective view of the distal portion of the stricture dilation device shown in FIG. 1B showing the actuator expanded.

FIGS. 1A-1C illustrate one exemplary embodiment of a dilation device 10 that is adapted to dilate a stricture within a lumen. The device 10 can have a variety of configurations, but in one exemplary embodiment it can include an elongate shaft 14 having a proximal end 14a coupled to a handle 14 and a distal end 14b adapted to be positioned within a lumen, and an actuator 16 coupled to a distal portion of the elongate shaft 14 and adapted to expand to dilate a stricture.

The handle 12 can have any configuration that allows a user to manually control the device 10, and in particular to control energy delivery to the actuator 16, as will be discussed in more detail below. As shown in FIG. 1A, the handle 12 has a generally elongate shape to facilitate grasping. The handle 12 can also include features and components to facilitate operation of the device 10. For example, in one exemplary embodiment, an energy source, such as a battery, can be disposed within the handle 12 for delivering energy to the actuator 16. Alternatively, the handle 12 can be adapted to be coupled to an energy source, such as an electrical outlet. The handle 16 can also include a mechanism that allows a user selectively activate and deactivate the delivery of energy to the actuator 16. For example, the handle 12 can include a button 20 that can be moved or pressed to deliver energy to the actuator 16, as shown in FIG. 1A. Alternatively, or in addition, the handle 12 can include a sliding lever or rotating dial that can be used to control the amount of energy being delivered, thereby allowing the amount of expansion of the actuator 16 to be controlled, as will be discussed in more detail below.

The elongate shaft 14 extending from the handle 12 can also have a variety of configurations, and the shape and the size of the elongate shaft 14 can vary depending upon the intended use of the device 10. In one exemplary embodiment, the elongate shaft 14 can have a generally cylindrical shape and it can be flexible to allow for insertion into the esophagus. The length of the shaft 14 can vary depending upon the particular procedure being performed. For example, where a stricture is dilated in a stoma, the shaft 14 can have a length in the range of about 4 feet to 6 feet. The elongate shaft 14 can also include various features to facilitate insertion through a lumen, such as a tapered distal tip 18. A person skilled in the art will appreciate that the shaft can be rigid, and it can have a variety of other configurations. For example, while not shown, the shaft 14 can include a lumen extending therethrough for providing access to a surgical site, such as for drug delivering, imaging, fluid flow, etc.

As previously indicated, the device 10 can also include one or more actuators coupled to the flexible elongate shaft 14 to effect stricture dilation. While the actuator(s) can have a variety of configurations, one suitable actuator is an electroactive polymer actuator. Electroactive polymers (EAPs), also referred to as artificial muscles, are materials that exhibit piezoelectric, pyroelectric, or electrostrictive properties in response to electrical or mechanical fields. In particular, EAPs are a set of conductive doped polymers that change shape when an electrical voltage is applied. The conductive polymer can be paired with some form of ionic fluid or gel using electrodes. Upon application of a voltage potential to the electrodes, a flow of ions from the fluid/gel into or out of the conductive polymer can induce a shape change of the polymer. Typically, a voltage potential in the range of about 1 V to 4 kV can be applied depending on the particular polymer and ionic fluid or gel used. It is important to note that EAPs do not change volume when energized, rather they merely expand in one direction and contract in a transverse direction.

One of the main advantages of EAPs is the possibility to electrically control and fine-tune their behavior and properties. EAPs can be deformed repetitively by applying external voltage across the EAP, and they can quickly recover their original configuration upon reversing the polarity of the applied voltage. Specific polymers can be selected to create different kinds of moving structures, including expanding, linear moving, and bending structures. The EAPs can also be paired to mechanical mechanisms, such as springs or flexible plates, to change the effect of the EAP on the mechanical mechanism when voltage is applied to the EAP. The amount of voltage delivered to the EAP can also correspond to the amount of movement or change in dimension that occurs, and thus energy delivery can be controlled to effect a desired amount of change.

There are two basic types of EAPs and multiple configurations for each type. The first type is a fiber bundle that can consist of numerous fibers bundled together to work in cooperation. The fibers typically have a size of about 30-50 microns. These fibers may be woven into the bundle much like textiles and they are often referred to as EAP yarn. In use, the mechanical configuration of the EAP determines the EAP actuator and its capabilities for motion. For example, the EAP may be formed into long strands and wrapped around a single central electrode. A flexible exterior outer sheath will form the other electrode for the actuator as well as contain the ionic fluid necessary for the function of the device. When voltage is applied thereto, the EAP will swell causing the strands to contract or shorten. An example of a commercially available fiber EAP material is manufactured by Santa Fe Science and Technology and sold as PANION™ fiber and described in U.S. Pat. No. 6,667,825, which is hereby incorporated by reference in its entirety.

Figure 2A:
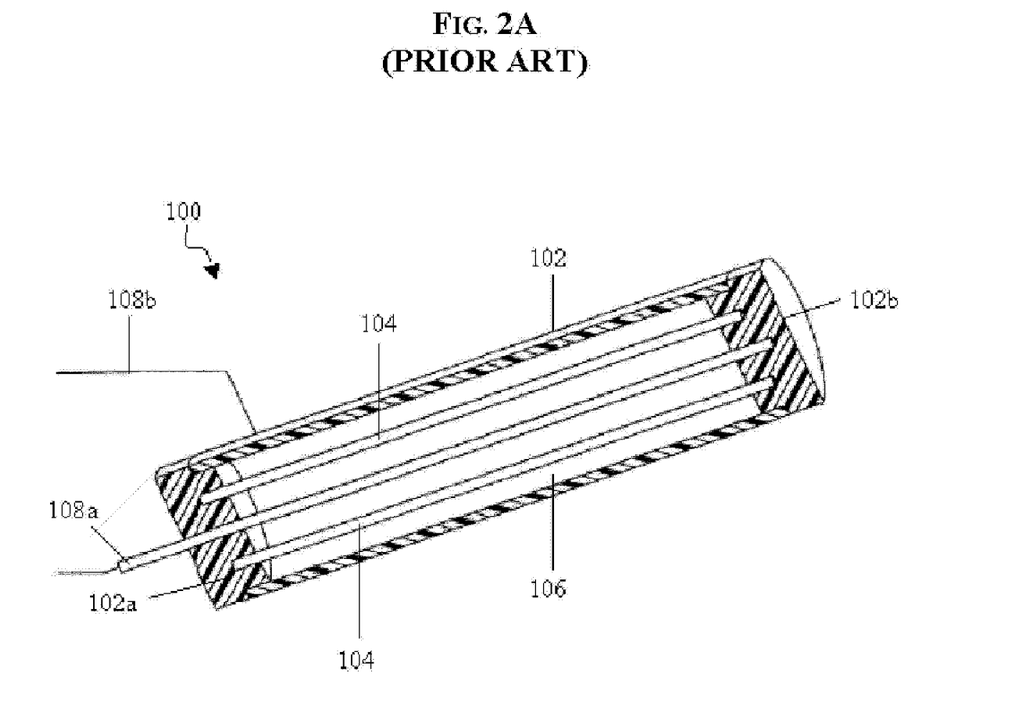
FIG. 2A is a cross-sectional view of a prior art fiber bundle type EAP actuator.
Figure 2B:
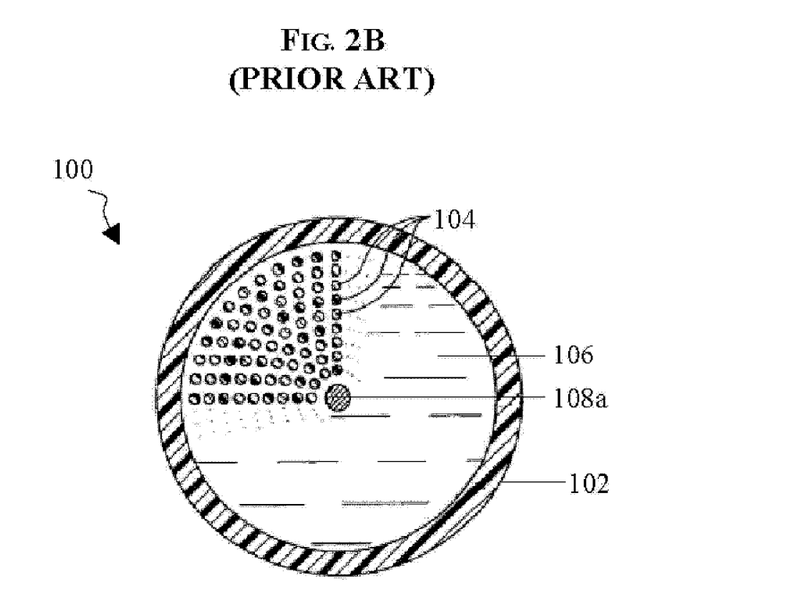
FIG. 2B is a radial cross-sectional view of the prior art actuator shown in FIG. 2A.

FIGS. 2A and 2B illustrate one exemplary embodiment of an EAP actuator 100 formed from a fiber bundle. As shown, the actuator 100 generally includes a flexible conductive outer sheath 102 that is in the form of an elongate cylindrical member having opposed insulative end caps 102a, 102b formed thereon. The conductive outer sheath 102 can, however, have a variety of other shapes and sizes depending on the intended use. As is further shown, the conductive outer sheath 102 is coupled to a return electrode 108a, and an energy delivering electrode 108b extends through one of the insulative end caps, e.g., end cap 102a, through the inner lumen of the conductive outer sheath 102, and into the opposed insulative end cap, e.g., end cap 102b. The energy delivering electrode 108b can be, for example, a platinum cathode wire. The conductive outer sheath 102 can also include an ionic fluid or gel 106 disposed therein for transferring energy from the energy delivering electrode 108b to the EAP fibers 104, which are disposed within the outer sheath 102. In particular, several EAP fibers 104 are arranged in parallel and extend between and into each end cap 102a, 120b. As noted above, the fibers 104 can be arranged in various orientations to provide a desired outcome, e.g., radial expansion or contraction, or bending movement. In use, energy can be delivered to the actuator 100 through the active energy delivery electrode 108b and the conductive outer sheath 102 (anode). The energy will cause the ions in the ionic fluid to enter into the EAP fibers 104, thereby causing the fibers 104 to expand in one direction, e.g., radially such that an outer diameter of each fiber 104 increases, and to contract in a transverse direction, e.g., axially such that a length of the fibers decreases. As a result, the end caps 102a, 120b will be pulled toward one another, thereby contracting and decreasing the length of the flexible outer sheath 102.

Another type of EAP is a laminate structure, which consists of one or more layers of an EAP, a layer of ionic gel or fluid disposed between each layer of EAP, and one or more flexible conductive plates attached to the structure, such as a positive plate electrode and a negative plate electrode. When a voltage is applied, the laminate structure expands in one direction and contracts in a transverse or perpendicular direction, thereby causing the flexible plate(s) coupled thereto to shorten or lengthen, or to bend or flex, depending on the configuration of the EAP relative to the flexible plate(s). An example of a commercially available laminate EAP material is manufactured by Artificial Muscle Inc, a division of SRI Laboratories. Plate EAP material, referred to as thin film EAP, is also available from EAMEX of Japan.

Figure 3A:
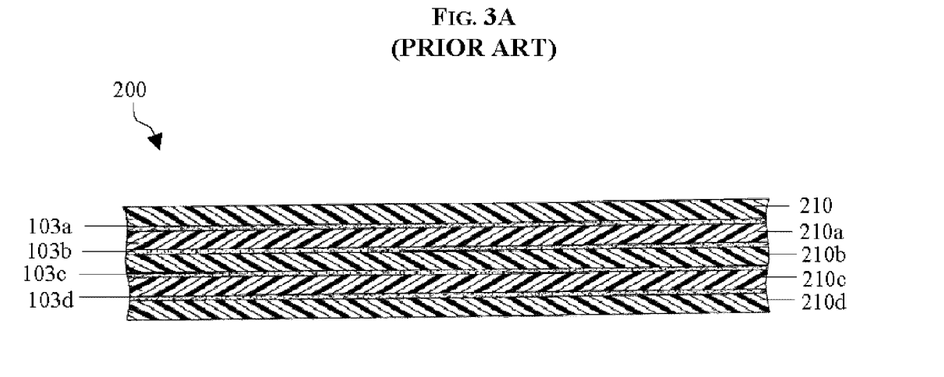
FIG. 3A is a cross-sectional view of a prior art laminate type EAP actuator having multiple EAP composite layers.
Figure 3B:
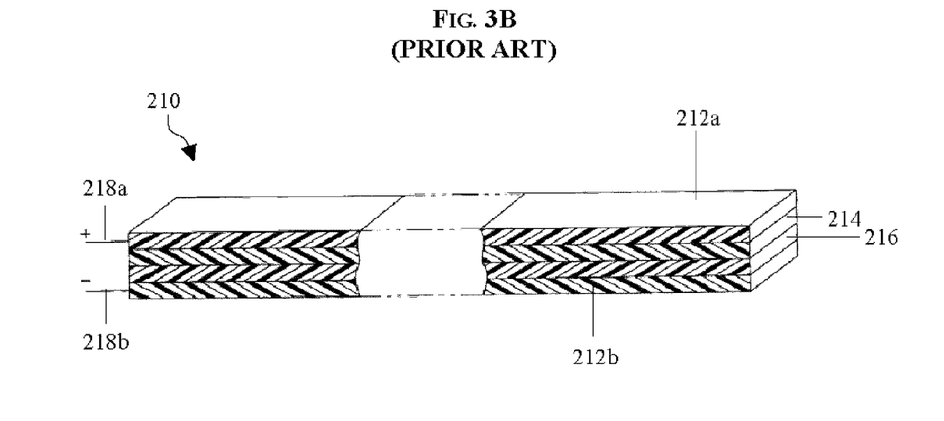
FIG. 3B is a perspective view of one of the composite layers of the prior art actuator shown in FIG. 3A.

FIGS. 3A and 3B illustrate an exemplary configuration of an EAP actuator 200 formed from a laminate. Referring first to FIG. 3A, the actuator 200 can include multiple layers, e.g., five layers 210, 210a, 210b, 210c, 210d are shown, of a laminate EAP composite that are affixed to one another by adhesive layers 103a, 103b, 103c, 103d disposed therebetween. One of the layers, i.e., layer 210, is shown in more detail in FIG. 3B, and as shown the layer 210 includes a first flexible conductive plate 212a, an EAP layer 214, an ionic gel layer 216, and a second flexible conductive plate 212b, all of which are attached to one another to form a laminate composite. The composite can also include an energy delivering electrode 218a and a return electrode 218b coupled to the flexible conductive plates 212a, 212b, as further shown in FIG. 3B. In use, energy can be delivered to the actuator 200 through the active energy delivering electrode 218a. The energy will cause the ions in the ionic gel layer 216 to enter into the EAP layer 214, thereby causing the layer 214 to expand in one direction and to contract in a transverse direction. As a result, the flexible plates 212a, 212b will be forced to flex or bend, or to otherwise change shape with the EAP layer 214.

Referring back to FIGS. 1A-1C, either type of actuator can be used to effect dilation of a stricture. However, in an exemplary embodiment, the actuator(s) is in the formed of an EAP laminate, or composite formed from multiple laminates. While the number and location of actuators can vary depending on the intended use, in the illustrate embodiment the elongate shaft 14 includes a single actuator 16 coupled to a distal end portion of the shaft 14 just proximal to the tapered tip 18. The actuator 16 can be mated to the shaft 14 using a variety of techniques, and the mating technique can depend on the type of actuator. Where the actuator 16 is an EAP laminate or composite actuator, the actuator 16 can be wrapped around and adhered to the shaft 14 using an adhesive or other mating technique. The orientation of the EAP actuator can be configured to allow the actuator 16 to expand radially and contract axially when energy is delivered thereto, thereby allowing a diameter of the actuator 16 to increase. While not shown, the actuator 16 can optionally be disposed within an inner lumen of the shaft and/or embedded within the walls of the shaft 14, or alternatively the actuator 16 can be formed integrally with the shaft 14. In use, energy can be delivered to the actuator 16 to cause the actuator to expand radially and contract axially. While various techniques can be used to deliver energy to the actuator 16, in one embodiment the actuator can be coupled to a return electrode and a delivery electrode that is adapted to communicate energy from an external power source to the actuator. The electrodes can extend through the inner lumen in the elongate shaft 14, be embedded in the sidewalls of the elongate shaft 14, or they can extend along an external surface of the elongate shaft 14.

Figure 4A:
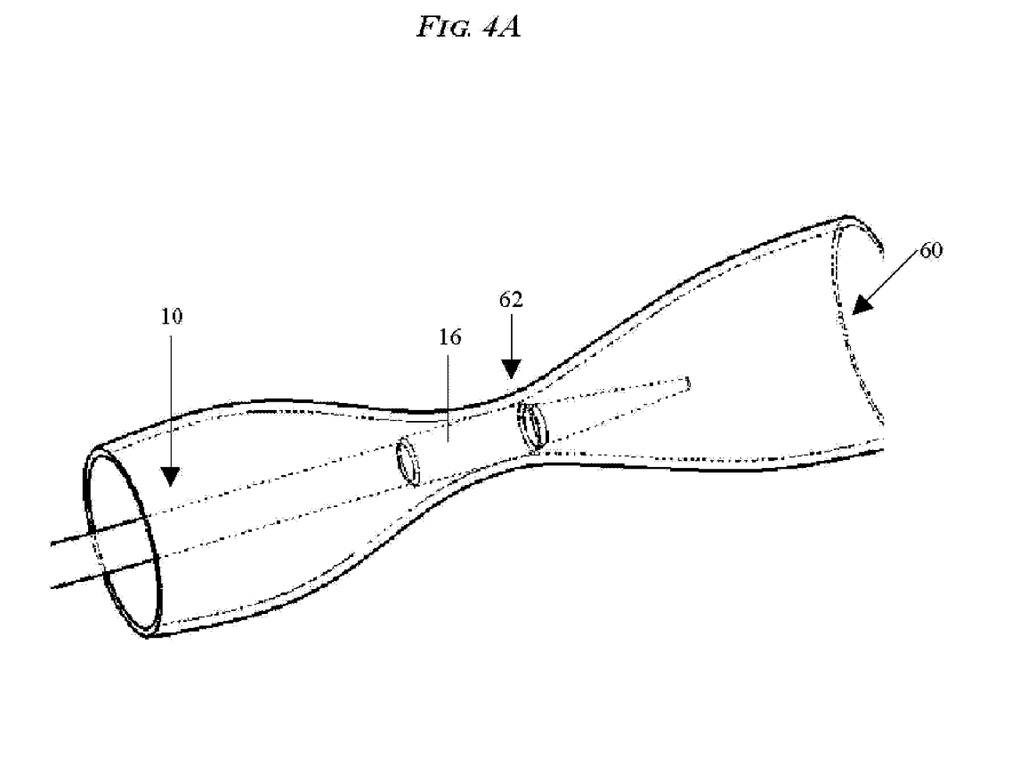
FIG. 4A is an illustration showing the stricture dilation device of FIG. 1A in use, showing the actuator disposed within a stricture.
Figure 4B:
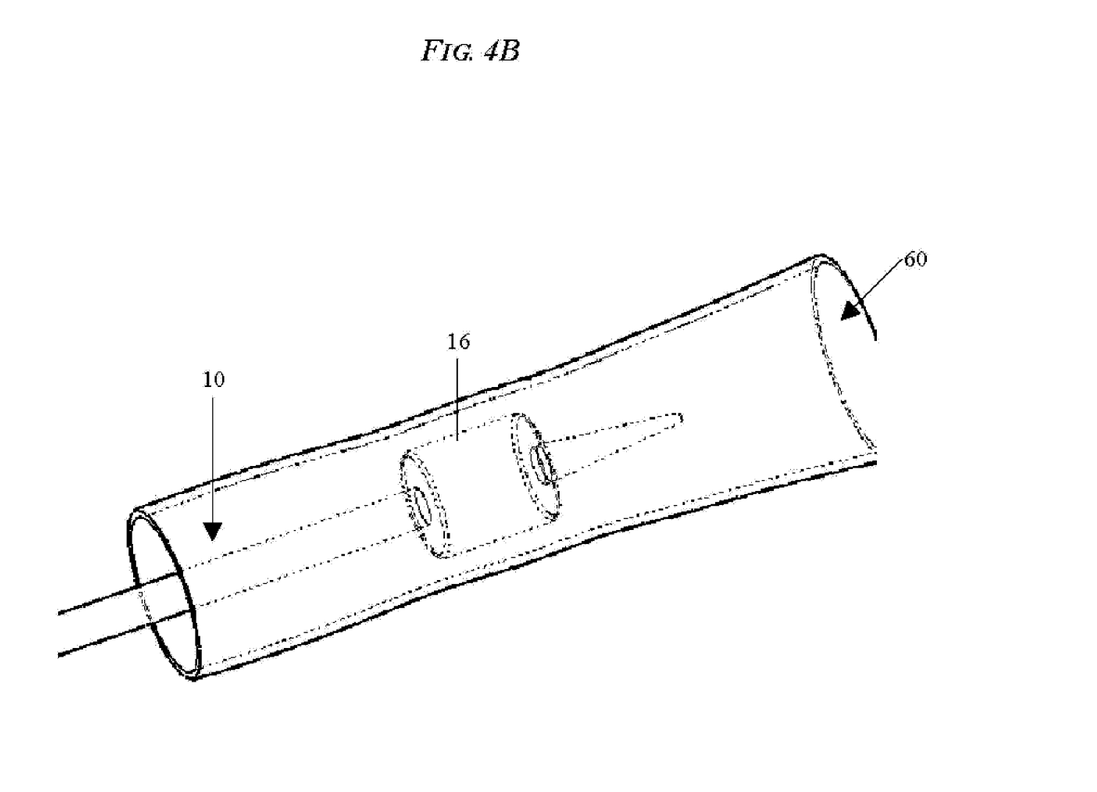
FIG. 4B is an illustration showing the stricture dilation device of FIG. 4A in use, showing the actuator expanded within the stricture to dilate the stricture.

FIGS. 4A and 4B illustrate one exemplary method for using the device 10 to dilate a stricture in a lumen. As shown, the device 10 can be inserted into a lumen 60 in the body with the actuator 16 being deactivated, i.e., in a resting configuration without energy being applied thereto. Once the stricture 62 is located, for example by imaging the lumen, the actuator 16 is positioned within the stricture. Energy can be then be delivered to the actuator 16 to cause the actuator 16 to radially expand, as shown in FIG. 4B, i.e., to increase a diameter of the actuator 16. The amount of radial expansion of the actuator 16 can be controlled by adjusting the amount of energy being delivered, and the radial expansion of the actuator 16 can be maintained so long as the energy is continuously supplied to the actuator 16. As a result of the radial expansion of the actuator 16, the actuator 16 will expand against the fibrous tissue of the stricture, causing the tissue to break and the stricture to dilate. Typically the actuator 16 can expand at least about 30% its size when energy is delivered thereto. For example, in certain exemplary embodiments the actuator 16 can have a diameter that ranges from about 16 mm in the unexpanded condition to about 25 mm in the expanded condition. The shape and size of the actuator 16 can, of course, vary depending on the intended use. Once the stricture is dilated, energy delivery to the actuator can be terminated to cause the actuator to return to its resting configuration. If the device includes more than one actuator formed thereon, other actuators can also be selectively activated and de-activated, either alone or in combination, to effect dilation.

One skilled in the art will further appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A tissue dilation device, comprising:
    a substantially flexible elongate shaft having a proximal end coupled to a handle and a distal end adapted to be positioned within a stricture formed in a lumen; and
    an integrally formed electroactive polymer actuator disposed around a distal portion of the flexible elongate shaft and adapted to radially expand upon delivery of electrical energy thereto to directly contact and dilate the stricture.

2. The device of claim 1, wherein the electroactive polymer actuator has a substantially cylindrical shape.

3. The device of claim 1, wherein the electroactive polymer actuator is positioned just proximal to the distal end of the flexible elongate shaft.

4. The device of claim 1, wherein the electroactive polymer actuator comprises a flexible conductive outer shell having an electroactive polymer and an ionic fluid disposed therein.

5. The device of claim 1, wherein the electroactive polymer actuator comprises at least one electroactive polymer composite having at least one flexible conductive layer, an electroactive polymer layer, and an ionic gel layer.

6. The device of claim 1, wherein the electroactive polymer actuator is adapted to radially expand at least about 30% in size when electrical energy is delivered thereto.

7. The device of claim 1, wherein the electroactive polymer actuator includes a return electrode and a delivery electrode coupled thereto, the delivery electrode being adapted to deliver electrical energy to the actuator from an energy source.

8. The device of claim 7, further comprising an energy source disposed within the handle and coupled to the delivery electrode.

9. The device of claim 1, wherein the flexible elongate shaft had a length that is in the range of about 4 feet to 6 feet.

10. The device of claim 1, wherein the electroactive polymer actuator has a diameter of about 16 mm in an unexpanded configuration, and a diameter of about 25 mm in an expanded configuration.

11. A device for dilating a stricture in a lumen, comprising:
a handle;
a flexible elongate shaft extending from the handle; and
an integrally formed electroactive polymer actuator disposed around a distal portion of the flexible elongate shaft and configured to radially expand when electrical energy is delivered thereto and to directly contact and dilate a stricture in a lumen.

12. The device of claim 11, wherein the distal portion of the flexible elongate shaft has a tapered distal tip adapted to be inserted through a stricture in a lumen.

13. The device of claim 11, wherein the electroactive polymer actuator is positioned just proximal to the distal end of the flexible elongate shaft.

14. The device of claim 11, wherein the electroactive polymer actuator comprises a flexible conductive outer shell having an electroactive polymer and an ionic fluid disposed therein.

15. The device of claim 11, wherein the electroactive polymer actuator comprises at least one electroactive polymer composite having at least one flexible conductive layer, an electroactive polymer layer, and an ionic gel layer.

16. The device of claim 11, wherein the electroactive polymer actuator is adapted to radially expand at least about 30% in size when electrical energy is delivered thereto.

17. The device of claim 11, wherein the electroactive polymer actuator includes a return electrode and a delivery electrode coupled thereto, the delivery electrode being adapted to deliver electrical energy to the electroactive polymer actuator from an energy source.

18. The device of claim 11, further comprising an energy source disposed within the handle and coupled to the delivery electrode.

19. The device of claim 11, wherein the flexible elongate shaft had a length that is in the range of about 4 feet to 6 feet.

20. The device of claim 11, wherein the electroactive polymer actuator has a diameter of about 16 mm in an unexpanded configuration, and a diameter of about 25 mm in an expanded configuration.

21. A method for dilating strictures, comprising:
inserting a substantially flexible elongate shaft into a lumen;
positioning an integrally formed electroactive polymer actuator disposed on a distal portion of the substantially flexible elongate shaft within a stricture formed in the lumen; and
delivering energy to the electroactive polymer actuator to cause the electroactive polymer actuator to expand radially to directly contact and increase a diameter of the stricture.

22. The method of claim 21, wherein the electroactive polymer actuator has a substantially cylindrical shape.

23. The method of claim 21, wherein the electroactive polymer actuator expands at least about 30% in size when electrical energy is delivered thereto.

24. The method of claim 21, wherein the lumen is an esophagus.

25. The method of claim 21, wherein the stricture is formed in a stoma.

* * * * *